(12) United States Patent
Pusiol

(10) Patent No.: US 7,292,033 B2
(45) Date of Patent: Nov. 6, 2007

(54) SENSOR ASSEMBLY AND METHOD FOR THE DETECTION OF SUBSTANCES BY NUCLEAR QUADRUPOLAR RESONANCE (NQR) AND IN PRESENCE OF ENVIRONMENTAL INTERFERENCE

(76) Inventor: Daniel J. Pusiol, Avda. Del Tajamar 255, Alta Gracia, Córdoba (AR) 5186

(*) Notice: Subject to any disclaimer, the term of this patent is extended or adjusted under 35 U.S.C. 154(b) by 6 days.

(21) Appl. No.: 10/972,876

(22) Filed: Oct. 25, 2004

(65) Prior Publication Data
US 2005/0116716 A1    Jun. 2, 2005

(30) Foreign Application Priority Data
Oct. 24, 2003    (AR) .............................. P030103887

(51) Int. Cl.
G01V 3/00    (2006.01)
(52) U.S. Cl. ...................................................... 324/307
(58) Field of Classification Search ................. 324/307, 324/309
See application file for complete search history.

(56) References Cited

U.S. PATENT DOCUMENTS

| | | | |
|---|---|---|---|
| 4,763,074 A * | 8/1988 | Fox .............................. 324/314 |
| 5,280,246 A * | 1/1994 | Takahashi et al. ........... 324/322 |
| 5,510,714 A * | 4/1996 | Takahashi et al. ........... 324/318 |
| 5,559,434 A * | 9/1996 | Takahashi et al. ........... 324/318 |
| 6,054,856 A | 4/2000 | Garroway et al. |
| 6,091,240 A * | 7/2000 | Smith et al. .................. 324/300 |
| 6,100,688 A * | 8/2000 | Smith et al. .................. 324/300 |
| 6,222,364 B1 * | 4/2001 | Smith et al. .................. 324/300 |
| 6,252,461 B1 * | 6/2001 | Raab ............................ 330/302 |
| 6,486,838 B1 | 11/2002 | Smith et al. |
| 6,552,634 B1 * | 4/2003 | Raab ............................ 333/216 |
| 6,914,432 B2 * | 7/2005 | Dumoulin et al. ........... 324/318 |

OTHER PUBLICATIONS

Agreev et al., "Composite pulses in nuclear quadrupole resonance", Molecular Physics, vol., 83, pp. 193-220 (1994).

(Continued)

Primary Examiner—Diego Gutierrez
Assistant Examiner—Dixomara Vargas
(74) Attorney, Agent, or Firm—Volpe and Koenig, P.C.

(57) ABSTRACT

A sensor assembly for the detection of substances by means of nuclear quadrupolar resonance (NQR) and in the presence of environmental interference. The sensor assembly has a transmitter $T_x$ which comprises excitation means which generate excitation signals and a switch connected at the outlet of the Transmitter. A first phase-shifted signal divider/adder is connected to the outlet of the switch. First and second sensor elements are connected to the respective outlets of the first phase-shifted signal divider/adder. First and second coupling circuits, preferably of common mode, are connected to the outlet of the first and second sensor elements, respectively. First and second amplifiers are connected to the outlets of the first and second coupling circuits, respectively. First and second bandpass filters are connected to the outlets of the first and second amplifiers, respectively. A second phase-shifted signal divider/adder is connected to the outlets of the first and second bandpass filters, respectively. A receiver $R_x$ is connected to the inlet of the second phase-shifted signal divider/adder. The method associated to the sensor assembly is also disclosed.

37 Claims, 2 Drawing Sheets

OTHER PUBLICATIONS

V.S. Grechishkin, "NQR device for detecting plastic explosives Mines and Drugs", Applied Physics, vol. A55, pp. 505-507 (1992).

D. Tomasi et al., "Fast optimization of a Biplanar Gradient Coil Set", Journal of Magnetic Resonance, 140: 325-339 (1999).

E.C. Caparelli et al., "Shielded biplanar Gradient Coil Design", Journal of Magentic Resonance Imaging, 9: 725-731 (1999).

G.V. Mozjuokhine, "The frequency offset effects of NQR of spin $I = 1$ for remote detection"; Z. Naturforschung, vol. 57a, pp. 297-303 (2002).

* cited by examiner

SENSOR ASSEMBLY AND METHOD FOR THE DETECTION OF SUBSTANCES BY NUCLEAR QUADRUPOLAR RESONANCE (NQR) AND IN PRESENCE OF ENVIRONMENTAL INTERFERENCE

BACKGROUND

The present invention refers to a method and sensor assembly for the detection of substances by means of nuclear quadrupolar resonance and in presence of environmental interference. More specifically, the invention refers to the detection of forbidden substances hidden in garments, particularly in shoes, or in luggage.

FIELD OF INVENTION

Nuclear quadrupolar resonance (NQR) is a radiofrequency spectroscopic technique frequently used for non-metallic chemical and physical materials analysis. The response generated by NQR is characteristic of the magnetic and electrical properties of resonant nuclei. The NQR phenomenon can only take place in some atoms (which nuclei exhibit non-null quadrupolar moment, i.e. spin $I>\frac{1}{2}$) and can be easily observed when such atoms are part of crystalline or amorphous materials. Thus, for instance, all those explosives containing chlorine and/or nitrogen are potentially detectable through this technique.

Technically, NQR is similar to the wide-known nuclear magnetic resonance (NMR), but the advantage thereof is that the object to be examined does not require its introduction into a strong and magnetic field. NQR signals of nitrogen in RDX and other explosives (see, for example, V. S. Grechishkin, "NQR device for detecting plastic explosives Mines and Drugs", Applied Physics, Vol. A55, pp 505-507 (1992)) have already been observed with a sensibility sufficient to form the basis of a detector which may be used in order to examine travel bags as well as closed postal parcels, personal carriers, etc. The nuclear quadrupolar resonance phenomenon on nitrogenous substances is mainly observed within the radiofrequency range, that is to say, explosives detection is done by means of radio waves, conveniently conditioned with special electronic devices. Each chemical compound conforming the explosive substance bears one or more unique resonance frequencies which distinguish such compound from the other compounds which exist in nature.

Electric and magnetic properties of atomic nuclei produce the NQR phenomenon. Nuclei with spherically non-symmetrical electric charge possess a quadrupolar electric moment. Other nuclear property consists of the possession of a magnetic moment, also known as nuclear spin. NQR originates upon the interaction between the nucleus electric quadrupolar moment and the (gradient of) electric field originated from the electric charges (or electrons) adjoining the nucleus.

Graphically, albeit not in a rigorous manner: when a quadrupolar nucleus experiments an electric field gradient originating from the atomic environment, this occurs as if different portions of the nucleus were experiencing a torque making them to precess (rotate) around the direction of the field gradient. This precession movement "drags" the nuclear magnetic moment. Should the sample be temporarily subject to a rotating magnetic field, in syntony with this precession, the nuclear magnetic moment orientation as regards the electric field gradient direction may be modified. Such oscillating electric field is readily achieved by placing the sample near a radiofrequency (RF) generator during a convenient period of time (typically on the order of microseconds) known as "RF pulse". Upon the termination of the pulse, the magnetization of the sample, which precesses with the resonance frequency, produces a detectable signal known as "free induction decay signal", usually named FID.

The above mentioned precession frequency depends on two parameters:

firstly it is proportional to the quadrupolar moment Q of the nucleus, which is related to the internal charge distribution of said nucleus. Q parameter is zero in those cases in which the nucleus charges distribution has a spherical symmetry, positive when the charges distribution is elongated along the main axis, and negative when it is flat relative to said axis. Symmetry properties of the nucleus require that a necessary condition for the nucleus Q to be different from zero is that the spin quantic number (ormagnetic quantic number) be higher than one half: $I>\frac{1}{2}$; and secondly, frequency is controlled by the main components of the electric field gradient sensed by the observed nucleus, q. For example, in the case of a nuclei system with spin $I=\frac{3}{2}$, quadrupolar coupling constant is defined as: $\upsilon Q=2\Pi e^2 gQ/h$, q being the maximum electric field gradient component generated by the electronic charge distribution at the location of the nucleus, Q the nucleus quadrupolar moment and h Planck's constant.

These definitions show that the resonance frequency value, which may be measured with high precision with any NQR experiment, is a characteristic magnitude of the molecule bearing the resonant nucleus—as if it were a "fingerprint". There exist in nature many different quadrupolar nuclei. Those commonly present in explosives are nitrogen, chlorine, potassium, sodium, etc. All of these nuclei are detected by routine in NQR spectrometers used in scientific research, as well as in the case of explosives. For example, it is possible to inspect the presence of different explosives or alkaloids by adjusting the detector to the characteristic frequence of said molecule, which must be—obviously—well known beforehand.

There have been detected since recent years several cases of prohibited and/or dangerous substances smuggled in footwear, particularly regarding explosives and alkaloids. It is necessary to restrain traffic of different kinds of dangerous substances, both in order to avoid terrorist attacks and the introduction thereof into high demand places such as certain prisons and correctional institutions. At present, garments inspection, particularly footwear, in order to search for a possible prohibited substance smuggling, is done by means of statistic samples of the population circulating through inspection points. Due to the generally large number of people to be registered, this is a bothersome, slow and conflict-generating operation which demands complicated logistics, further representing a waste of time and economic resources.

Efforts have been carried out in order to detect smuggling through different types of spectroscopic analysis. It has been particularly shown that methods involving nuclear quadrupolar resonance (NQR) have been successfully employed for the detection of explosives and alkaloids in luggage, as well as for the detection of anti-personal and anti-tank mines.

In order to accomplish the first application there have been developed volumetric sensors of different geometry which however share the basic idea of introducing into a coil the object to be inspected, generally a piece of luggage, and by means of a NQR pulse spectrometer, to irradiate the sample with different pulses sequences "in resonance" with the substance which detection is sought. It is to be remarked that in this case the excitation-detection process is accomplished via the electromagnetic field generated within the coil interior volume, within which the luggage or object to be inspected is placed.

As regards the second application, in which the explosive is under the floor surface, surface sensors are used. Such sensors comprise antennas, which may take the form of coils of differing geometries (planar solenoidal, spiral, with ferrite nuclei, etc.), the irradiation-detection process being produced by the electromagnetic field generated at the volume external thereto.

Regarding the volumetric application, both the sensor and the object to be inspected are introduced into a volume with an adequate electromagnetic shield, in order to protect the signal originating from the substance sought for from the external electromagnetic noise. That is to say, the sensor, in such conditions, is immune to environmental electromagnetic noise. This is not possible in the case of surface sensors.

Surface sensors basic devices comprise two coils with loops wound in opposite directions, which are located one over the other or one beside the other on the same plane, always within a short distance between them, and they are electrically connected both in series and in parallel. In this device far away electromagnetic noises are annulled and the object to be inspected is placed nearer to one of the antennas than to the other, so that the NQR signal is induced more intensely in one of them.

U.S. Pat. No. 6,054,856 discloses a noise-immune antenna to be used in nuclear magnetic resonance or nuclear quadrupolar resonance. Transmission line bears an electrically continuous conductor through the antenna, and a shield divided in such a position that the antenna is electrically balanced, thus reducing environmental noise effects and the effects of the nearby conductors. Nothing therein shows or suggests the fact of simultaneously analyzing two or more substances which are placed at different places.

U.S. Pat. No. 6,486,838 discloses an apparatus and method directed to analyze a forbidden substance based on nuclear quadrupolar resonance with two antennas. A first antenna is used to send an excitation signal to a potential forbidden substance which is located near said first antenna. Said signal preferably approaches the resonance frequency of the substance under analysis. Said antenna then detects the response of said sent excitation signal, along with the interference signal originated from the external environment. Both antennas are conformed by coils. A second antenna farther away from said potential forbidden substance is only used in order to detect the interference signal from the external environment. Said first and second antennas, in being wound in opposite directions, cause the attenuation of the interference signal detected by both of them, as regards the excitation signal which is sent by one of the antennas. However, the authors of the above patent state that it is not possible to detect signals when the forbidden substance is placed at an equidistant distance between them. When both antennas are active, the response to the emitted excitation signals will induce two push-pull signals, which mutually annul themselves in the same way the electromagnetic noise is annulled. Column 6, lines 33 to 42 and column 8, lines 30 to 38, particularly mention the possibility of both antennas to be active in the emission and reception of signals intended to detect this kind of substances, provided the sample to be inspected is small as compared to the observation field of each antenna, so that the risk of cancellation among the antennas is small. That is to say, said document contemplates a geometrical limitation and nothing therein teaches or suggests the detection of a forbidden substance in more than one place at the same time, as would be the case if such substances were hidden in both shoes, for instance.

The forbidden substance to be detected may be placed outside or inside the coil volume; also, the case could be an hybrid situation as regards the above, i.e., partially inside and partially outside. Internal volume of the coil is intended to mean that space subtended by the peripherical surface and those planes perpendicular to the main symmetry axis thereof. All of the volume not contained as described is considered external or, more simply "the exterior of the coil". Geometric shapes of coils herein referred to are those generally well known, for example circular, rectangular, hexagonal, etc. Flat coils, such as those composed of wires or strips of appropriated metal and provided the electric current flow proceeds through a single plane, will have no internal volume, i.e., the sample may only be placed at the exterior of the coil. Where the current circulates through a concave plane, it shall be understood as internal volume (or merely "interior of the coil") that which is subtended by the volume resulting from the intersection of the current plane and an imaginary plane perpendicular to the symmetry axis of the coil.

It is particularly expected from smugglers to pretend the transportation of some kind of forbidden substance in his/her two shoes. The sensor assembly according to the invention will simultaneously inspect both shoes, achieving the highest possible efficiency, and also increasing the inspection speed and the accuracy of the corresponding result. Further, the individual will only be required to stand on the sensors without the need of any surrounding shielding.

In order to carry out such inspection the above technique, known as nuclear quadrupolar resonance (NQR), is used, which is known as the response (echo) of a certain substance which contains some quadrupolar nucleus, at a radiofrequency pulse (RF) applied "in resonance". The technique employed is harmless to the environment, luggage and people. Its application is direct, it does not require any previous preparation of the objects to be inspected. The detection process implies very fast routine inspections which may be directly carried out on a pedestrian path, the passenger to be stopped during few seconds on a specially demarked area while he/she is examined. It typically takes a few seconds to verify the existence of explosives and/or other dangerous substances in shoes or carried pieces of luggage, without it being necessary to open them or contact them in any manner with mechanical and/or palpation tools. No ionizing radiations are used, thus avoiding any danger to luggage or individuals. Each sensing assembly is automatic, thus allowing an easy operation which does not require highly trained personnel who should have to make subjective decisions.

The present invention resolves the problem referred to the detection of plastic explosives and other forbidden substances which can not be easily detected by means of conventional inspection techniques, as those based on X-ray apparatuses; or those using more sophisticated means starting from trace materials which may have remained "contaminating" the external surface of the object containing it. As regards the first technique, the invention has the additional advantage of being fully automatic, i.e., it does not depend on the operator's ability to interpret images of relatively low contrast and further, it does not use ionizing radiation.

Regarding the second methodology, the main advantage of the present invention is represented by the speed and safety with which it inspects luggage. Particularly, it would be very easy to saturate and consequently neutralize a trace-analyzing machine by an excess of false positives, by simply spreading very small quantities of forbidden substances on the floor of the airport and/or facility to be guarded, thus contaminating most of the shoes of passengers and/or passers by, when actually no substance is being carried.

SUMMARY

The present invention specially applies to the detection of the NQR signal of $^{14}$N nuclei in explosives such as: TNT, RDX PBX, HMX Pentrite, Compound B, ammonium nitrate, Octol, other mixtures composed of such materials as for example Compound B and Semtex; and in alkaloids such as cocaine base, cocaine hydrochloride, heroin, etc.

Accordingly, it is an object of the present application a sensor assembly for the detection of hidden forbidden substances by means of nuclear quadrupolar resonance (NQR) and in presence of environmental interferences, said sensor assembly comprising:

a transmitter $T_X$ which comprises excitation means which generate excitation signals;

a switch connected at the outlet of said transmitter Tx;

a first phase-shifted signal divider/adder, connected to the outlet of said switch;

first and second sensor elements, connected to the respective outlets of said first phase-shifted signal divider/adder;

first and second coupling circuits, preferably of common mode, connected to the outlet of said first and second sensor elements, respectively;

first and second amplifiers connected to the outlets of said first and second coupling circuits, respectively;

first and second bandpass filters connected to the outlets of said first and second amplifiers, respectively;

a second phase-shifted signal divider/adder, connected to the outlets of said first and second bandpass filters, respectively; and a receiver $R_X$ connected to the outlet of said second phase-shifted signal divider/adder.

It is also an object of the invention a method for the to detect signals originated from forbidden detection of hidden forbidden substances by means of nuclear quadrupolar resonance (NQR) and in presence of environmental interferences, which method uses the above sensor assembly and comprises the following steps:

to generate excitation signals at a frequency approaching the resonance frequency of the forbidden substances to be detected;

to direct said excitation signals towards a switch;

to divide said excitation signals at a first phase-shifted divider/adder;

to emit said excitation signals by means of a first and a second antennas; substances and environmental interference induced into each antenna;

to amplify and filter said induced signals;

to combine said induced signals at a second phase-shifted divider/adder; and to add said induced signals and send them to the receiver $R_X$.

Preferably, excitation signals are radiofrequency pulses and amplifiers are radiofrequency matching amplifiers.

In those cases where coils are wound in the same sense it will be necessary to include first and second signal dividers/adders with a 0°-180° phase-shift; and should said coils be wounded in opposite directions, it will be necessary to include first and second signal dividers/adders with a 0°-0° phase-shift, as will be discussed below.

BRIEF DESCRIPTION OF THE DRAWING(S)

The invention will be more apparent with the aid of the following figures.

DETAILED DESCRIPTION OF THE PREFERRED EMBODIMENT(S)

Figure 1:
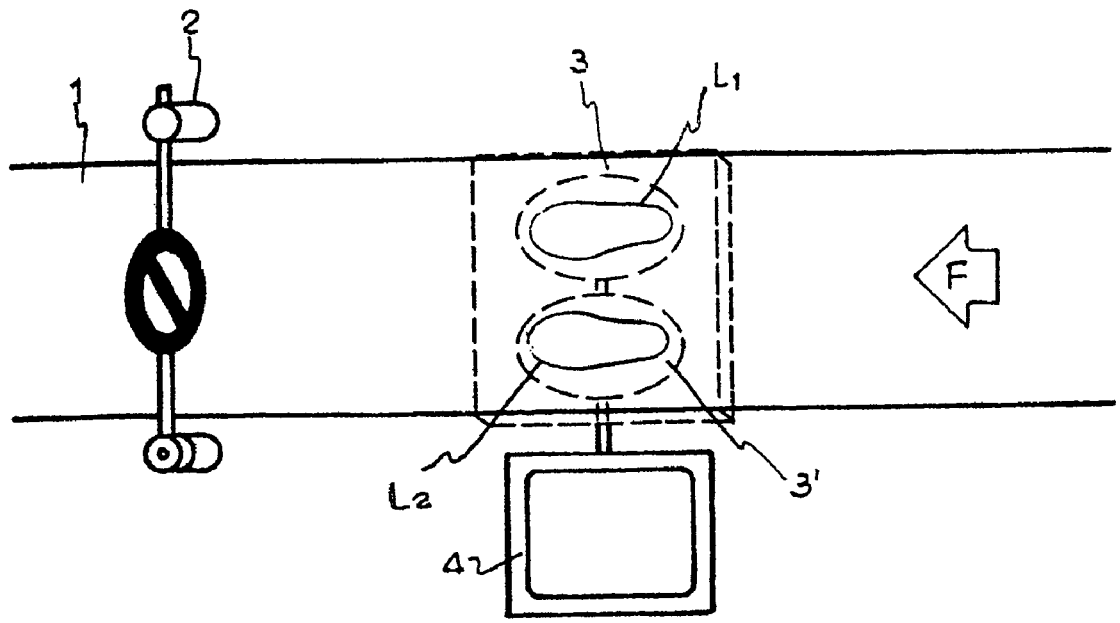
FIG. 1 shows a schematic view of a detection arrangement which uses the sensor assembly according to the present invention.
Figure 2:
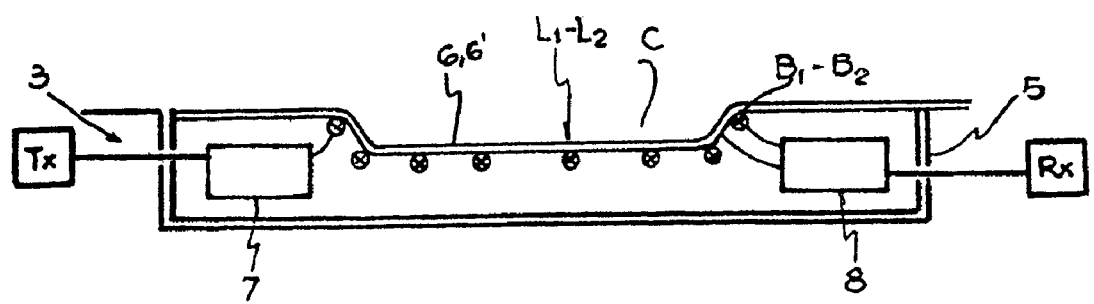
FIG. 2 shows a section of the by-passers path corresponding to the detecting arrangement of FIG. 1.

FIG. 1 shows a schematic view of a detection arrangement comprising a by-passers path 1 which includes a sensor assembly 3 fixed to the floor. According to a preferred embodiment, said floor bears ellipsoidal concave grooves 3' for each foot; two antennas $L_1$ and $L_2$ are arranged around said grooves. However, the floor need not possess said grooves, or if they exist, they may have another geometric configuration that a technician of average knowledge in the art will opportunely evaluate. Said antennas $L_1$ and $L_2$ are placed under the floor level and are enclosed by an electric field shielding 5, as illustrated in FIG. 2 and which will be discussed below. Spectrometer 4 is in charge of automatic measurements and, lastly, in the case of a negative detection regarding forbidden substances, by-passers may move on—as shown by arrow F—upon the aperture of gate 2. This detection arrangement is autonomous and may operate without the need of specialized personnel.

According to the detection needs, said sensor assembly 3 may also form part of a portable device or may be mounted on walls, crossing-gates or the like.

FIG. 2 shows a section of a by-passers path 1 on which shoes to be analyzed will rest. In the case of this preferred embodiment, antennas $L_1$ and $L_2$ are conformed by ellipsoidal detecting coils $B_1, B_2$ arranged on a concave plane C made on the floor, which has been so designed that the current density of spirals is optimized in order to obtain a magnetic field as uniform as possible throughout the volume expected to be taken by the forbidden substance to be detected. A transmitter $T_x$, generates excitation signals, preferably consisting of RF radiofrequency pulses, with a frequency approaching that of the nuclear quadrupole resonance of the forbidden substance to be detected. Said pulses are sent towards a sensor element 6, 6' through an outlet block 7.

Then, the environmental interference signals and those induced by the presence of forbidden substances are sent through an outlet block 8 to a receiver $R_x$.

All of the sensor assembly 3 is shielded at the laterals and bottom thereof by means of copper or aluminum sheets at least 0.5 mm thick. Top electric shielding is carried out as usual, that is to say, by means of a thin layer of non-ferromagnetic material, such as copper or aluminum. Metallized plastic may also be used, which material is commonly known as "antistatic", the most adequate according to this invention being that which is built with metallized epoxy resins and may form part of the by-passer's path itself. Metal thickness should not be higher than what is known as "skin depth" (J. D. Jackson, "*Electrodinámica*

*Clásica*", Editorial Alambra, Madrid, Buenos Aires, Mexico, 1966), in order to avoid an excessive attenuation of the magnetic field both regarding excitation and detection, and for it to provide at the same time shielding against electric fields. Top shielding is placed between antenna $L_1$, $L_2$ and the object to be detected, in a position adequate for the generation of eddy currents, which effect is that of reducing the quality factor Q. In order to obtain this effect adequate geometry cuts are done (forming bars, circles, etc.) on the shielding metallic film. Antennas $L_1$ and $L_2$ may also be constructed in an "auto-shield" geometry which may be, for example, biplanar (see D. Tomasi, E. C. Caparelli, H. Panepucci and B. Foerster, "Fast optimization of a Biplanar Gradient Coil Set", Journal of Magnetic Resonance, 140 325 (1999); E. C. Caparelli, D. Tomasi and H. Panepucci, "Shielded biplanar Gradient Coil Design", Journal of Magnetic Resonance Imaging, 9, 725 (1999)).

Figure 3:
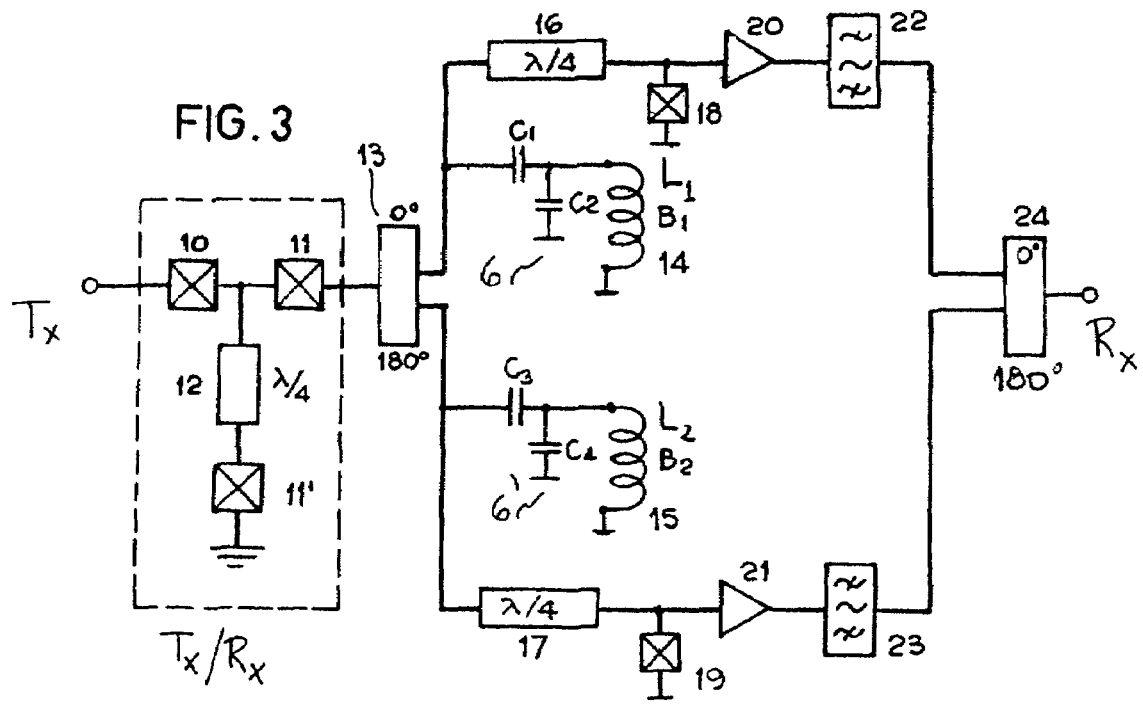
FIG. 3 shows a first embodiment of a sensor assembly comprising two antennas comprised of coils which are wound in the same direction.

FIG. 3 is a detailed illustration of the electric circuit of sensor assembly 3 according to one of the embodiments of the present invention. First and second sensor elements 6, 6' are conformed by tuning circuits which configuration may be in parallel, in series or balanced. Said configurations may be devised by a technician of average knowledge in the art. For the particular case of what is depicted by FIG. 3, it is shown a tuning circuit in parallel. Said first and second sensor elements 6, 6' respectively include antennas $L_1$ and $L_2$, conformed by coils $B_1$ and $B_2$ which are wound in the same sense, said antennas $L_1$ and $L_2$ respectively connected in parallel to capacitors $C_1$, $C_2$; $C_3$, $C_4$. Optionally, said first and second sensor elements 6, 6' may include coupling coils in order to accomplish a more efficient manner of impedance adaptation with transmitter $T_x$ and receiver $R_x$.

Electric operation of sensor assembly 3 is as follows: radiofrequency (RF) pulses generated by the excitation elements included in transmitter $T_x$ are sent to a switch, preferably a Transmitter/Receiver switch $T_x/R_x$ ($T_x/R_x$ switch). Said $T_x/R_x$ switch is conformed by sets of cross diodes pairs 10, 11 and 11' and a quarter-wave line ($\lambda$4) 12. The function of said $T_x/R_x$ switch is to isolate transmitter $T_x$ from the sensor assembly 3 when the first does not actuate, preventing the passage of environmental interference or noise from transmitter $T_x$, to receiver $R_x$, during the detection period. Other designs for the $T_x/R_x$ switch are also possible, such as the known circulators composed of fraction waveguides with working wavelength.

Then, radiofrequency pulses are divided at a first 0-180° phase-shifted signal divider/adder 13, reversing the phase of one of them. This is a key procedure regarding the operation of an antenna arrangement which is wounded in the same sense in simultaneous detection processes which are the object of this invention. Radiofrequency pulses which have been already divided enter each tuning circuit and particularly each antenna $L_1$ and $L_2$. In this way, both antennas $L_1$ and $L_2$ emit radiofrequency RF pulses in phase opposition in a frequency which approaches that of the nuclear quadrupolar resonance (NQR) of the forbidden substance to be detected. During the detection process there may be induced electromotive forces in each of the antennas $L_1$ and $L_2$ which are the product of the detection of any forbidden substance and environmental interference.

Induced electromotive forces are then amplified in first and second radiofrequency matching amplifiers 20,21 and filtered in first and second bandpass filters 22,23 before entering a second 0-180° phase-shifted signal divider/adder 24, wherein one of the induced quadrupolar signals originating from one of the detected substances is again phase-shifted at 180° in order to be in phase with the other induced quadrupolar signal resulting from the other detected substance and which remains non-phase-shifted. Accordingly, both induced quadrupolar signals, once again in phase, are added, increasing the detection sensitivity. On the other hand, the environmental interference signal is induced in both phased $L_1$ and $L_2$ antennas. Then, when passing through the second 0°-180° phase-shifted signal divider/adder 24, one of the environmental interference signals induced into one of the antennas is phase-shifted 180° with respect to the environmental interference signal induced in the other antenna. Thus, both induced environmental interference signals are cancelled.

Said first and second radiofrequency matching amplifiers 20 and 21 are protected by quarter-wave lines 16 and 17 and by cross diodes 18 and 19 respectively, conforming first and second coupling circuits, preferably of common mode.

Figure 4:
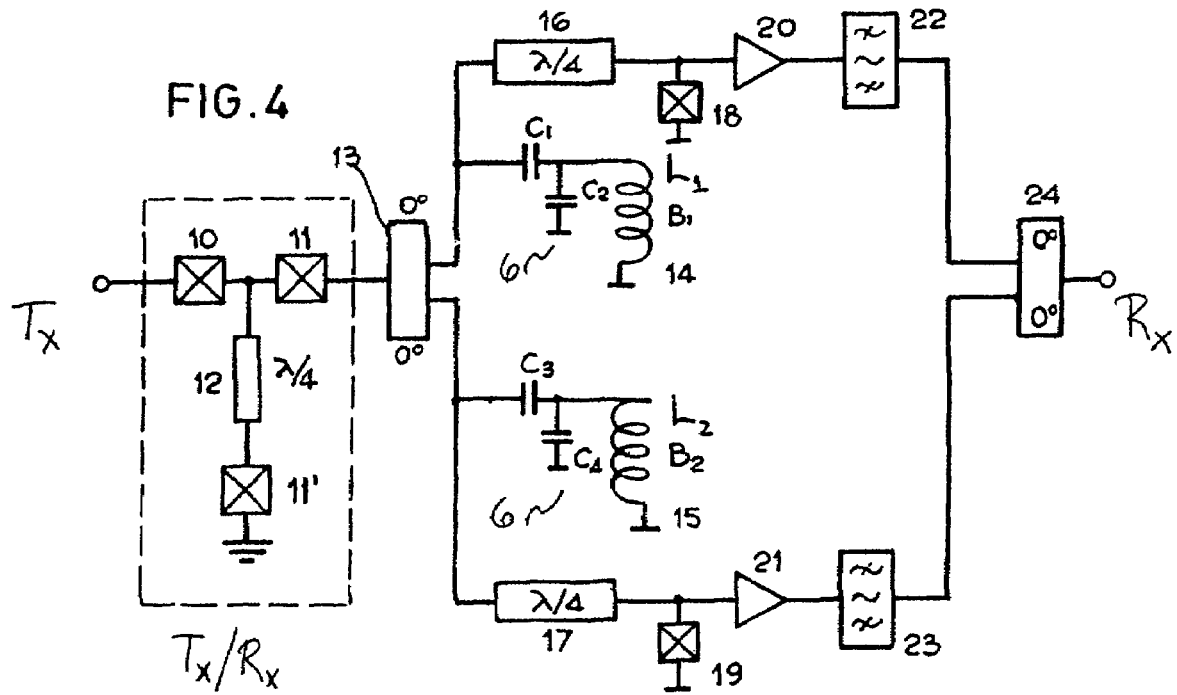
FIG. 4 shows a second embodiment of a sensor assembly comprising two antennas comprised of coils which are wound in opposite directions.

FIG. 4 illustrates a variant of the example depicted by FIG. 3, wherein coils $B_1$ and $B_2$ associated to the emission/reception antennas $L_1$ and $L_2$ are wounded in opposite directions. In this particular case, the only variant respecting the first embodiment illustrated by FIG. 3 is that the first and second signal dividers/adders 13, 24 are 0°-0° phase-shifted. The opposite wounding itself of the coils causes cancellation of the signal induced by environmental interference upon combination, as the interference originates from a common source. As regards forbidden substances, both $L_1$ and $L_2$ antennas emit counter-phase radiofrequency pulses due to the opposite wounding of their respective coils $B_1$ and $B_2$, with which the electromotive forces induced as a response to said radiofrequency pulses are phased again, due to the fact that they are collected by antennas with opposing wounds, and thence their values are summed.

Electronics (not shown) associated with the sensor assembly according to the invention comprises elements for the connection, isolation and protection of the sensor assembly 3, receiver $R_x$ and transmitter $T_x$.

On the other hand, there exist diverse pulse sequences which may be used to accomplish this invention. We are making reference to the SLSE sequence: Spin-Locked Spin Echo. This consists of irradiating the sample with a first RF pulse of an amplitude such as to be able to re-orient magnetization of quadrupolar nuclei at a 90' angle and with a 0° phase for the synthesized signal generator. After a time $\tau$ has elapsed, a second RF pulse is applied, this time of double duration or able to re-orient sample 180° and with a 90° phase with respect to the first pulse one. At the exactly same period $\tau$ as from the termination of the second RF pulse the spin echo appears. Later another 180° pulse with phase 90° is applied and the second echo appears, with a magnitude slightly lower than the first one. Later, a third pulse is applied and the third echo appears—its magnitude always slightly lower than the preceding one—and so on until n echoes are collected (typically 1000 echoes). "Detection signal" means the collection of the amplitudes of all of the digitalized echoes summed together. In many practical cases it is possible to replace both the first and the second RF pulse by the so called "composite pulses" (see Agreev et al., "Composite pulses in nuclear quadrupole resonance", Molecular Physics, vol. 83, pp. 193-220 (1994)), in order to significantly increase the detection efficiency.

A second detection sequence is that known as SORC (Strong Off-Resonance Comb) (see G. V. Mozjuokhine, "The frequency offset effects of NQR of spin I=1 for remote detection"; Z. Naturforschung, vol. 57a, pp. 297-303 (2002)). This sequence consists of composite pulses of different amplitudes and phases which are equispaced in time. The detection signal is constructed by digitally adding by means of a computer several hundreds or thousands of the NQR signals which precede each composite pulse of the SORC sequence.

In all of these pulses sequences, the reference frequence may be changed during the step of the spin echo signal detection. This operation is carried out through a change of the direct digital synthetizer—DDS— frequency, and same is actuated by a pulse from the pulses programmer. It is to be understood that implementation of said change, in our circuit case, lasts a few nanoseconds. During the step of quadrature detection a "beat" of the spin echo is obtained, which is synchronic at the moment the echo signal is digitalized during the respective stage. Accordingly the result is that the echo frequencies content is increased by an amount: $\Delta = v_o - v_{ref}$, i.e. equal to the difference between the nuclear precession frequency (which is equal to that of the radiation in the exact resonance condition) and the frequency of the reference at the detection time. This trick enables displacing —within the sequences spectrum—the echo signal as collected at resonance conditions, adding a frequencies content to it. Indeed, when in resonance condition (or also in that of radiation in resonance) the echo obtained at the end of the stage of phase-sensitive detection and in quadrature, it only possesses very low frequency components. Now, upon changing the reference sequence by a known number, the "beaten echo" condition is attained, which condition bears an externally controllable frequency content; in practice it is generally situated within the range of the tenths and even hundreds of KHz. As the signal-to-noise ratio (SNR) increases with the content of predominant frequencies of the echo, through the reference signal frequency displacement at the detector in quadrature one may digitalize a signal with a remarkable improvement as regards the signal-to-noise ratio. This innovation may be applied to all known pulses sequences, and particularly to those mentioned above, and may be applied simultaneously with the procedure known as "phase cycling". This procedure allows the elimination of both i) noise effects at the base line and ii) coherent noise signals (for more details see E. Fukushima and S. B. W. Roeder "Experimental Pulse NMR: A Nuts and Bolts approach", Addison-Wesley Publishing Co., Reading, Mass., USA (1981)).

What is claimed is:

1. A sensor assembly for the detection of substances by means of nuclear quadrupolar resonance (NQR) and in the presence of environmental interference, said sensor assembly comprises:

a transmitter $T_x$ which comprises excitation means which generate excitation signals, a switch connected at an outlet of said Transmitter $T_x$;

a first phase-shifted signal divider/adder, connected to an outlet of said switch, said first phase-shifted signal divider/adder divides the excitation signals and shifts the phase of one of the divided signals by 0°-180° or 0°-0°;

first and second sensor elements, connected to respective outlets of said first phase-shifted signal divider/adder;

first and second coupling circuits, preferably of common mode, connected to respective outlets of said first and second sensor elements;

first and second amplifiers connected to respective outlets of said first and second coupling circuits;

first and second bandpass filters connected to respective outlets of said first and second amplifiers;

a second phase-shifted signal divider/adder, connected to respective outlets of said first and second bandpass filters, said second phase-shifted divider/adder shifts the phase of one of two induced quadrupolar signals by either 0°-180° or 0°-0° such that both of said quadrupolar signals are in phase and adds said quadrupolar signals; and a receiver Rx connected to an outlet of said second phase-shifted signal divider/adder.

2. Sensor assembly according to claim 1, characterized in that excitation signals are radiofrequencies pulses.

3. Sensor assembly according to claim 1, characterized in that said amplifiers are radiofrequency matching amplifiers.

4. Sensor assembly according to claim 1, characterized in that it is surrounded by a shielding.

5. Sensor assembly according to claim 4, characterized in that lateral and bottom shielding thereof is comprised of copper or aluminum sheet at least 0.5 mm thick.

6. Sensor assembly according to claim 4, characterized in that its top shielding is conformed by a thin layer of non-ferromagnetic or metallized plastic material.

7. Sensor assembly according to claim 6, characterized in that the top shielding is placed between the antenna and the object to be detected, in a position appropriate for preventing the generation of eddy currents.

8. Sensor assembly according to claim 4, characterized in that said shielding comprises sections of appropriate geometry.

9. Sensor assembly according to claim 1, characterized in that said first and second sensor elements are tuning circuits.

10. Sensor assembly according to claim 9, characterized in that said tuning circuits adopt the parallel, serial or balanced configurations.

11. Sensor assembly according to claim 9, characterized in that said first and second sensor elements respectively include first and second emission/reception antennas $L_1$ and $L_2$, preferably of auto-shielded geometry, said antennas $L_1$ and $L_2$, respectively connected in parallel to capacitors $C_1$, $C_2$, $C_3$, and $C_4$.

12. Sensor assembly according to claim 11, characterized in that said first and second emission/reception antennas $L_1$ and $L_2$ are conformed by coils $B_1$ and $B_2$, respectively.

13. Sensor assembly according to claim 12, characterized in that said coils $B_1$ and $B_2$ are wounded in the same sense.

14. Sensor assembly according to claim 12, characterized in that said coils $B_1$ and $B_2$ are wounded in opposite senses.

15. Sensor assembly according to claim 11, characterized in that said first and second antennas are connected in series.

16. Sensor assembly according to claim 11, characterized in that said first and second antennas are connected in parallel.

17. Sensor assembly according to claim 11, characterized in that it is fixed to a floor which bears ellipsoidal and concave grooves, around said grooves said first and second antennas are arranged.

18. Sensor assembly according to claim 17, characterized in that said first and second antennas are of ellipsoidal shape, and are arranged on a concave plan C which is designed in such a way that the current density at the spirals on the concave surface is optimized in order to attain a magnetic field as uniform as possible throughout all of the volume expected to be occupied by the forbidden material to be detected.

19. Sensor assembly according claim 1, wherein one of the respective outlets of said first phase-shifted signal divider/adder is a 0° outlet to which said first sensor element is connected.

20. Sensor assembly according to claim 1, wherein another of the respective outlets of said first phase-shifted signal divider/adder is a 180° outlet to which second sensor element is connected.

21. Sensor assembly according to claim 1, wherein said second phase-shifted divider/adder includes a 0° inlet to which said first bandpass filter is connected.

22. Sensor assembly according to claim 1, wherein said second phase-shifted divider/adder includes a 180° inlet to which said second bandpass filter is connected.

23. Sensor assembly according to claim 1, characterized in that it is mounted on walls, crossing-gates or the like.

24. Sensor assembly according to claim 1, characterized in that it is portable.

25. Sensor assembly according to claim 1, characterized in that said switch is a Transmitter/Receiver switch $T_x/R_x$, ("$T_x/R_x$ switch") which comprises sets of cross diodes and a quarter-wave line ($\lambda/4$).

26. Sensor assembly according to claim 1, wherein one of the respective outlets of said first phase shifted divider/adder is a 0° outlet to which said first sensor element is connected.

27. Sensor assembly according to claim 1, wherein another of the respective outlets of said first phase-shifted signal divide/adder is a 0° outlet to which said second sensor element is connected.

28. Sensor assembly according to claim 1, wherein said second phase-shifted signal divider/adder includes a 0° inlet to which said first bandpass filter is connected.

29. Sensor assembly according to claim 1, wherein said second phase-shifted signal divider/adder includes a 0° inlet to which said second bandpass filter is connected.

30. A method for the detection, by means of nuclear quadrupolar resonance (NQR) and in the presence of environmental interference, of hidden forbidden substances, which method uses the sensor assembly according to claim 1, characterized in that it comprises the following steps:
 to generate excitation signals at a frequency approaching the resonance frequency of the forbidden substances to be detected;
 to direct said excitation signals towards a switch;
 to divide said excitation signals at a first phase-shifted signal divider/adder;
 to emit said excitation signals by means of a first and a second antennas;
 to detect signals originated from forbidden substances and environmental interference induced into each antenna;
 to amplify and filter said induced signals;
 to combine said induced signals at a second phase-shifted signal divider/adder; and
 to add said induced signals and send them to the receiver $R_x$.

31. A method according to claim 30, characterized in that said excitation signals are radiofrequency pulses.

32. A method according to claim 30, characterized in that said induced signals amplification is carried out in radiofrequency matching amplifiers.

33. A method according to claim 30, characterized in that filtering of said excitation signals is carried out by means of bandpass filters.

34. A method according to claim 30, characterized in that said switch is a Transmitter/Receiver switch $T_x/R_x$ ("$T_x/R_x$ switch").

35. A method according to claim 30, characterized in that when coils conforming said first and second antennas are wound in the same sense, said first and second phase-shift signal dividers/adders are phase-shifted 0°-180° after the division of the radiofrequency pulses and the combination of said induced signals respectively.

36. A method according to claim 30, characterized in that when coils conforming said first and second antennas are wound in opposite senses, said first and second phase-shifted signal dividers/adders are phase-shifted 0°-0° after the division of the radiofrequency pulses and the combination of said induced signals respectively.

37. A method according to claim 30, characterized in that said excitation signals are generated by excitation means included in a transmitter $T_x$.

* * * * *